US010738069B2

(12) United States Patent
Ritt et al.

(10) Patent No.: US 10,738,069 B2
(45) Date of Patent: *Aug. 11, 2020

(54) METHOD FOR ISOLATING NUCLEIC ACIDS

(71) Applicant: QIAGEN GmbH, Hilden (DE)

(72) Inventors: Christoph Ritt, Hilden (DE); Martin Horlitz, Hilden (DE); Markus Sprenger-Haussels, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/723,435

(22) Filed: Oct. 3, 2017

(65) Prior Publication Data

US 2018/0244707 A1 Aug. 30, 2018

Related U.S. Application Data

(63) Continuation of application No. 12/995,348, filed as application No. PCT/EP2009/003364 on May 12, 2009, now Pat. No. 9,809,612.

(30) Foreign Application Priority Data

May 30, 2008 (EP) ..................... 08009941

(51) Int. Cl.
*C07H 1/08* (2006.01)
*C12N 15/10* (2006.01)
(52) U.S. Cl.
CPC ........... *C07H 1/08* (2013.01); *C12N 15/1006* (2013.01)
(58) Field of Classification Search
CPC .............................. C07H 1/08; C12N 15/1006
See application file for complete search history.

(56) References Cited

U.S. PATENT DOCUMENTS

| | | |
|---|---|---|
| 5,945,525 A | 8/1999 | Uematsu et al. |
| 6,383,393 B1 | 5/2002 | Colpan et al. |
| 2002/0119478 A1 | 8/2002 | Umansky et al. |
| 2005/0054847 A1 | 3/2005 | Madden et al. |
| 2005/0059024 A1 | 3/2005 | Conrad |
| 2005/0164241 A1 | 7/2005 | Hahn et al. |
| 2006/0269929 A1 | 11/2006 | Hall et al. |
| 2007/0026435 A1 | 2/2007 | Templer |
| 2007/0106071 A1 | 5/2007 | Yamashita et al. |
| 2007/0190535 A1 | 8/2007 | Hall et al. |
| 2008/0207889 A1 | 8/2008 | Sprenger-Hasels et al. |
| 2011/0130558 A1 | 6/2011 | Ritt et al. |

FOREIGN PATENT DOCUMENTS

| | | |
|---|---|---|
| DE | 43 21 904 A1 | 1/1995 |
| EP | 0 389 063 B1 | 8/1997 |
| EP | 1 690 938 A1 | 8/2006 |
| EP | 1 873 241 A1 | 1/2008 |
| EP | 2 128 169 A1 | 12/2009 |
| EP | 2 285 816 B1 | 4/2015 |
| WO | 95/01359 A1 | 1/1995 |
| WO | 95/21849 A1 | 8/1995 |
| WO | 97/34015 A1 | 9/1997 |
| WO | 99/61603 A1 | 12/1999 |
| WO | 01/71732 A2 | 9/2001 |
| WO | 2004/108925 A1 | 12/2004 |
| WO | 2005/012487 A2 | 2/2005 |
| WO | 2005/012523 A1 | 2/2005 |
| WO | 2005/089929 A2 | 9/2005 |
| WO | 2006/084753 A1 | 8/2006 |
| WO | 2007/140417 A2 | 12/2007 |
| WO | 2009/146776 A2 | 12/2009 |

OTHER PUBLICATIONS

Moore et al., Current Protocols in Molecular Biology, 2002, Supplement 59, John Wiley & Sons, Inc., p. 2.1.1-2.1.10. (Year: 2002).*
Bianchi et al., "Isolation of fetal DNA from nucleated erythrocytes in maternal blood," *Proc. Natl. Acad. Sci. USA* 87:3279-3283 (May 1990).
Chan et al., "Size Distributions of Maternal and Fetal DNA in Maternal Plasma," *Clinical Chemistry* 50(1):88-92 (2004).
DNAclear™ Purification Kit—Product Sheet, Ambion®, ThermoFisher Scientific (1 page).
GenBank, NCBI Reference Sequence: NM_001289726.1 (69 pages) (Dec. 14, 2015).
Giacona et al., "Cell-free DNA in human blood plasma: length measurements in patients with pancreatic cancer and healthy controls," *Pancreas* 17(1):89-97 (1 page) (Abstract) (Jul. 1998).
Kieselgel, aus Wikipedia, der freien Enzyklopädie, https://de.wikipedia.org/wiki/Kieselgel (8 pages) (with English version) (Dec. 10, 2015).
Li et al. "Size Separation of Circulatory DNA in Maternal Plasma Permits Ready Detection of Fetal DNA Polymorphisms," *Clinical Chemistry* 50(6):1002-1011 (2004).
Li et al., "Cell-Free DNA in Maternal Plasma—Is It All a Question of Size?" *Ann N.Y. Acad. Sci.* 1075:81-87 (2006).
Melzak et al., "Driving Forces for DNA Adsorption to Silica in Perchlorate Solutions," *Journal of Colloid and Interface Science* 181:635-644 (1996).
Notice of Opposition corresponding to European Patent Application No. EP2285816, (38 pages) dated Dec. 15, 2015.

(Continued)

*Primary Examiner* — Jonathan S Lau
(74) *Attorney, Agent, or Firm* — Seed IP Law Group LLP

(57) ABSTRACT

The invention relates to a method and kits for isolating and/or purifying nucleic acids, in particular, short-chain nucleic acids, from a nucleic acid containing starting material, characterised by the following method steps: (a) bonding the nucleic acids to a nucleic acid bonding support material, wherein the starting material is brought into contact with the nucleic acid bonding support material in the presence of at least one chaotropic compound and preferably isopropanol, wherein the isopropanol is present in a concentration of ≥15% (v/v) and ≥35% (v/v), (b) optional elution of the bonded nucleic acids from the nucleic acid bonding support material. Said method is particularly suitable for the purification of foetal DNA from maternal blood.

22 Claims, 9 Drawing Sheets

(56) References Cited

OTHER PUBLICATIONS

Notice of Opposition corresponding to European Patent Application No. EP2285816, (33 pages) dated Dec. 27, 2015.
Notice of Opposition corresponding to European Patent Application No. EP2285816, (43 pages) dated Dec. 28, 2015.
QIAquick® Spin Handbook, Qiagen®, (44 pages) (Mar. 2008).
Steinberger et al., "Extracellular DNA in Single- and Multiple-Species Unsaturated Biofilms," *Applied and Environmental Microbiology* 71(9):5404-5410 (Sep. 2005).
Vergleichsversuche, reference D14 (4 pages), cited in Notice of Opposition corresponding to European Patent Application No. EP2285816 dated Dec. 15, 2015.

* cited by examiner

Fig. 9

| Protocol | Binding buffer - example | Total volume of sample [ml] | Binding buffer volume added [ml] | GuHCl [mol/l] | Isopropanol [%] |
|---|---|---|---|---|---|
| 1-step | B3 | 22.32 | 13.32 | 4.00 | 20.00 |
| | B4 | 22.32 | 13.32 | 3.50 | 30.00 |
| | B5 | 22.32 | 13.32 | 3.00 | 40.00 |
| | B6 | 22.32 | 13.32 | 2.50 | 50.00 |
| | B7 | 22.32 | 13.32 | 2.00 | 60.00 |
| | B8 | 22.32 | 13.32 | 1.50 | 70.00 |
| | B9 | 22.32 | 13.32 | 1.00 | 80.00 |
| | B11 | 22.32 | 13.32 | 0.00 | 100.00 |

METHOD FOR ISOLATING NUCLEIC ACIDS

The present application is a continuation application of U.S. application Ser. No. 12/995,348 filed Feb. 10, 2011, now pending, which is a U.S. national phase application of PCT/EP2009/003364 filed May 12, 2009, which claims priority to EP Application No. 08009941.9 filed May 30, 2008. U.S. application Ser. No. 12/995,348 is herein incorporated by reference in its entity.

The present invention relates to a method for isolating and/or purifying nucleic acids, in particular short-chain nucleic acids.

Nucleic acids such as DNA and RNA are normally isolated from plant, animal or human materials and from cell cultures or virus cultures according to a uniform basic pattern: the starting materials containing nucleic acids are first disrupted—partly by using protein-degrading enzymes. The individual constituents can be removed in subsequent steps using a large variety of methods. In addition, nucleic acids may be isolated from sample materials in which they are present in a free form, i.e. they are not inside cells. Thus it is possible for free nucleic acids to occur in artificial sample mixtures but also in natural samples such as blood, for example. Such freely circulating nucleic acids are also referred to as extracellular nucleic acids.

Most of the prior art methods for purifying said nucleic acids are based on either of the two following principles of removal:

The classical methods are based on a one-step process which comprises carrying out an extraction after a buffer which contains a chaotropic agent in most cases and an organic extractant—usually phenol and/or chloroform—have been added. The undesired accompanying substances are discarded together with the organic phase. The nucleic acids retained in the aqueous phase may then be removed by separating the phases and thereby isolated. The important disadvantage of this procedure, aside from the use of toxic and harmful substances such as phenol and/or chloroform, is that of water-soluble substances remaining as contaminants in the aqueous nucleic acid solution and having to be removed in further, very time-consuming purification steps.

In view of these disadvantages, an alternative process has therefore established itself in the prior art, which process is based on selective adsorption of nucleic acids to solid support materials such as silicon dioxide, for example. The nucleic acid-containing starting material is lysed, if necessary, and contacted with said support material under defined conditions to enable the nucleic acids to bind to the support material; where appropriate, washing steps are carried out. Subsequently and optionally the nucleic acid bound to the support is eluted from the support material by means of a suitable buffer.

U.S. Pat. No. 5,234,809 (Boom), for example, discloses a method for isolating nucleic acids, which is suitable for a multiplicity of different uses. It describes a method for isolating nucleic acids from nucleic acid-containing starting materials by incubating said starting material with a chaotropic buffer and a DNA-binding solid phase. The chaotropic buffers effect, if necessary, both lysis of the starting material and binding of the nucleic acids to the solid phase. Said method is well suited in order to isolate nucleic acids from relatively small sample quantities. WO 93/11221 also describes a method which is based on a similar principle.

Many methods of purifying nucleic acids have been disclosed in the prior art that comprise combining a solid phase with a chaotropic buffer. Since long-chain nucleic acids bind to the solid phase at least as well as, but in most cases considerably better than, short-chain nucleic acids (for example of less than 1000 guanidinium, 500 bp or even 300 bp in length) in all of the known methods, the prior art methods are not suitable for efficiently purifying short-chain nucleic acids or even enriching them over the long-chain nucleic acids.

The poor suitability for purifying short-chain nucleic acids can presumably be attributed to the fact that binding of said short-chain nucleic acids to the support material is inferior to that of long-chain nucleic acids (for example genomic DNA). A large part of short-chain nucleic acids is therefore lost in most of the common purification processes, and short-chain nucleic acids are not present or underrepresented among the purified nucleic acids. For certain applications, however, isolating short-chain nucleic acids or enriching them over long-chain nucleic acids is specifically desired.

In order to enrich preferably short-chain nucleic acids or to separate short-chain nucleic acids from long-chain nucleic acids, various principles have been used previously in the prior art. DE 10 2006 045 391, for example, describes a method for removing long nucleic acids from short nucleic acids, which comprises applying the sample several times to specially designed solid phases. Another method is based on the use of special binding buffers which contain citric acid salts rather than chaotropic salts in order to bind in this way short-chain nucleic acids in particular (WO 2007/065934).

Purification/enrichment of short-chain nucleic acids (RNA and DNA) is crucially important to various fields of application. One area in which short-chain nucleic acids play a central part is prenatal diagnostics. The blood of pregnant women contains, in addition to endogenous freely circulating DNA, also freely circulating DNA of the fetus. It is assumed that the fetal DNA which circulates freely in the blood of pregnant women differs in its size from the freely circulating DNA of the mother. While the average length of maternal freely circulating DNA is often more than 500 bp, a majority of the fetal freely circulating DNA is markedly smaller and on average less than 500 bp in length. This difference in size between the fetal and the maternal nucleic acids could be exploited in order to be able to enrich and therefore investigate in more detail fetal DNA, if suitable purification methods were available. Utilizing the freely circulating DNA of fetal origin for prenatal diagnostics would be advantageous over classical methods such as amniocentesis or chorionic villus sampling in that it will not be dangerous for the fetus and would therefore bear fewer risks. However, the quantities of freely circulating DNA of fetal origin in the blood are very low. Depending on the stage of the pregnancy, 1 ml of blood contains between 20 and 260 copies of fetal DNA. The concentration of freely circulating fetal DNA is thus low but still higher than the concentration of freely circulating fetal cells. There is also the problem of the concentration of the freely circulating fetal DNA being extremely low in comparison with freely circulating maternal DNA, and consequently only a fraction of the genetic material originates from the fetus when total freely circulating DNA is isolated from maternal blood; the majority of the isolated genetic material is from the mother. The high background of maternal DNA in many cases impedes the detection of fetal gene sections, and in some cases the sensitivity even of detection methods as sensitive as realtime PCR is not sufficient for enabling the fetal DNA to be detected.

The methods previously employed for isolating freely circulating DNA from maternal blood often purify fetal and maternal DNA to the same extent, thereby preserving the unfavorable ratio of fetal to maternal DNA—the fetal DNA makes up only a fraction of the total DNA. Up to now, fetal DNA has not been enriched over the maternal DNA. In addition, purification of the fetal nucleic acids has regularly been inferior, since short-chain nucleic acids are often caught less well during purification. Since they are not caught as well during purification, their concentration in the purified sample is then relatively lower than in the starting sample. Efficient purification or even specific enrichment of the short-chain extracellular nucleic acids such as, for example, fetal DNA would be advantageous, however, because this would substantially increase the sensitivity and therefore reliability of prenatal diagnostics based on freely circulating fetal DNA.

The present invention is therefore based on the object of providing a method for isolating and/or purifying nucleic acids, which is capable of efficiently isolating/purifying extracellular nucleic acids and in particular also short-chain nucleic acids. Another object of the invention is to provide a method for isolating fetal DNA from maternal blood, which allows said fetal DNA to be effectively isolated and/or enriched.

The object is achieved in the present application by a method for isolating and/or purifying nucleic acids, in particular short-chain nucleic acids, from a nucleic acid-containing starting material, characterized by the following method steps:
(a) binding nucleic acids to a nucleic acid-binding support material by contacting the starting material with said nucleic acid-binding support material in the presence of a chaotropic compound and an alcohol, preferably isopropanol, said alcohol being present at a concentration of ≥5% (v/v) and preferably ≤40% (v/v), preferably ≤35% (v/v) and more preferably ≤32% (v/v);
(b) optionally removing the bound nucleic acids from the nucleic acid-binding support material.

According to the method of the invention, the nucleic acids are immobilized to the support material under specific reaction conditions. Two components are crucial for effective binding of the short-chain nucleic acids to the support material, namely at least one chaotropic compound and a branched and/or unbranched alcohol. According to the invention, it is particularly important to choose the correct alcohol concentration which is ≥5% (v/v) in the sample mixture during binding to the support material. Preference is given, however, to the alcohol concentration being higher and therefore being ≥15, in particular ≥19% (v/v). Short-chain nucleic acids have been shown to bind very well to the support material when the correct alcohol concentration has been chosen. A lower alcohol concentration can be balanced to a certain extent by increasing the concentration of chaotropic substances. There is therefore an interaction between the alcohol concentration and the concentration of chaotropic compounds, which will be discussed hereinbelow. Adjusting the concentration of the alcohol according to the invention causes short-chain nucleic acids in particular to be bound efficiently and therefore caught during purification.

According to one embodiment, the alcohol concentration is in a range from approx. 19 to 40% (v/v), since short-chain nucleic acids and particularly DNA can be bound and therefore isolated particularly well within this range. Depending on the fine adjustment of the binding conditions, this may also enable the short-chain nucleic acids to be enriched over the long-chain nucleic acids. This advantageous enrichment effect is achieved in particular with an alcohol concentration of between 25 and 40% (v/v), 25 and 35% (v/v), 25 to 32% (v/v) and 28 to 32% (v/v). Under these conditions, the short-chain nucleic acids bind better and therefore preferably to the support material than the long-chain nucleic acids, as the examples also demonstrate. Binding of the nucleic acids is also influenced by the concentration of chaotropic compounds. Choosing a relatively high concentration of chaotropic compounds enables even relatively low alcohol concentrations to be employed.

According to a preferred embodiment which is particularly suitable for effectively isolating/purifying extracellular nucleic acids from a biological sample, the alcohol concentration in step (a) is within a range of ≥15% and ≤25% (v/v). In step (a), for example, the concentration of the alcohol in the mixture may be from approx. 18 to 20% (v/v). Experiments have demonstrated that even at these low alcohol concentrations nucleic acids of different lengths and also short-chain nucleic acids can be purified efficiently and, as a result, a broad size range is effectively caught. In order to ensure that the short-chain nucleic acids are readily caught, the chaotropic compound in step (a) should be at a sufficiently high concentration. The concentration of the chaotropic compound in step a) is therefore ≥2 mol/l. The concentration of chaotropic compound that must specifically be employed, in order to bind also the short-chain nucleic acids effectively, depends on the strength of the chaotropic compound employed. Thus, using a relatively weak chaotropic compound such as guanidinium hydrochloride, for example, requires a higher concentration than the use of a relatively strong chaotropic compound such as guanidinium thiocyanate, for example. Suitable strongly chaotropic compounds which promote binding of the short-chain nucleic acids even at relatively low alcohol concentrations may be selected based on the "Hofmeister series". According to the latter, strongly chaotropic anions are $NO_3^-$, $ClO_4^-$, $SCN^-$, $NCS^-$, and $Cl_3CCOO^-$. Examples of strongly chaotropic cations are $Ba^{2+}$ and guanidinium. Chaotropic compounds that are preferably employed are thiocyanates, isothiocyanates and/or perchlorates, in particular guanidinium thiocyanate or guanidinium isothiocyanate. These strongly chaotropic compounds are preferably employed in combination with relatively low alcohol concentrations of ≤25% (v/v). Suitable concentrations are ≥2.0 mol/l and ≤3.1 mol/l.

Washing steps may be carried out optionally. The nucleic acids bound to the support material are then removed from said support material, for example eluted in a manner known per se if recovery of the short-chain nucleic acids is desired. The nucleic acids isolated/enriched according to the invention may then be processed further in the known manner, i.e. analyzed, for example. Depending on the planned subsequent further processing or analysis, however, it is likewise possible to use the nucleic acids bound to the support material and thus without elution. The method may also be employed for removing nucleic acids from a sample.

The method of the invention can be carried out by way of a 1-step method. The advantage of a 1-step method is that of achieving usually a higher yield of nucleic acids (overall); only a small proportion of nucleic acids are lost during purification. Since the short-chain nucleic acids can effectively be bound to the support material and thereby isolated/enriched by the 1-step variant of the method of the invention, isolation/enrichment of the short-chain nucleic acids carried out in this way is already sufficient for many applications. A 1-step method is also particularly convenient for the user because it can be carried out rapidly and easily. As the comparative experiments shown in the examples prove, the 1-step method of the invention for isolating short-chain nucleic acids is distinctly superior to the methods disclosed in the prior art because the method of the invention can effectively isolate short-chain nucleic acids with good yields and in some cases even enrich the short-chain nucleic acids over the long-chain nucleic acids. The 1-step method is also particularly suitable for effectively purifying extracellular nucleic acids from a sample, in particular a bodily fluid such as in particular plasma or serum.

For particular uses, it is advantageous to enrich the short-chain nucleic acids over the long-chain nucleic acids as efficiently as possible; the short-chain nucleic acids should be recovered without or with very little background of long-chain nucleic acids. In this case, it is desirable to purify as few long-chain nucleic acids as possible. In order to achieve this in a particularly effective manner, according to one embodiment of the method of the invention, the actual isolation steps a) and optionally b) for removing/eluting the short-chain nucleic acids are preceded by a step (x) by which the long-chain nucleic acids are efficiently depleted. The preceding depletion of the long-chain nucleic acids enables short-chain nucleic acids to be recovered in a particularly pure form.

A corresponding improved method for isolating and/or purifying short-chain nucleic acids from a nucleic acid-containing starting material has, according to the invention, the following method steps:
  (x) binding nucleic acids to a nucleic acid-binding support material by contacting the starting material with said nucleic acid-binding support material in the presence of at least one chaotropic compound and at least one branched and/or unbranched alcohol, said alcohol being present at a concentration of ≤25% (v/v);
  (a) binding the breakthrough/supernatant from step (x) to a nucleic acid-binding support material by contacting said breakthrough/supernatant from step (x) with said nucleic acid-binding support material in the presence of at least one chaotropic compound and at least one branched and/or unbranched alcohol, the concentration of said alcohol being ≥5% (v/v) and preferably ≤40% (v/v), preferably ≤35% (v/v) and more preferably ≤32% (v/v);
  (b) optionally eluting the bound nucleic acids from the nucleic acid-binding support material.

According to this 2-step variant of the method of the invention, the actual isolation steps a) and b) for isolating/purifying the short-chain nucleic acids are preceded by step (x) which efficiently depletes the long-chain nucleic acids. The binding step (x) comprises binding the nucleic acids to the support material in the presence of chaotropic compounds and a branched and/or unbranched alcohol. The binding conditions and in particular the concentration of the alcohol in the whole sample during binding are again crucial for efficient depletion of the long-chain nucleic acids. The alcohol concentration in step (x) is ≤30% (v/v), and is preferably even ≤25% (v/v).

Surprisingly, an alcohol concentration around 25% (v/v) has been shown to be able to reverse the size selectivity. Long- and/or longer-chain nucleic acids are preferably bound to the support material below 25% (v/v), preferably below 20% (v/v), if the concentration of chaotropic compounds is chosen accordingly (see below). Under these conditions, the short-chain nucleic acids do not bind or bind more poorly to the support material and are therefore in the breakthrough/supernatant (depending on the support material employed). In the subsequent steps a) and optionally b), the short-chain nucleic acids are then isolated and thus enriched from the breakthrough/supernatant of step (x), which contains particularly the short-chain nucleic acids.

According to one embodiment, steps a) and b) of the 1-step method (see above) are very similar to steps a) and b) of the 2-step method and/or they are virtually identical. Ultimately, in the 2-step method, the breakthrough/supernatant from step (x) is used instead of the nucleic acid-containing starting material. Therefore, the same preferred conditions apply to steps a) and b) of the 2-step method as described in connection with the 1-step method. The preceding step (x) ultimately effects in addition a depletion of the long-chain nucleic acids, so that at least a lower amount thereof is present in the breakthrough/supernatant. If desired, the long-chain nucleic acids may, in the case of the 2-step method, likewise be eluted from the support material bound in step (x) and used further for different purposes.

As discussed, the type and concentration of the chaotropic compound influence the binding of the nucleic acids and in particular the efficiency of binding of the short-chain nucleic acids. If, therefore, the concentration of alcohol in the preceding step (x) and in the subsequent step (a) is the same or virtually the same, either a lower concentration of chaotropic compounds and/or a weaker chaotropic compound is employed in step (x) than in step (a). This, in turn, can result in depletion of the long-chain and thus enrichment of the short-chain nucleic acids. A suitable example of a weaker chaotropic compound which may be employed in step (x) is guanidinium hydrochloride, for example.

Various materials and in particular biological materials may be employed as nucleic acid-containing starting materials. These include, for example, viruses, phages, and cells such as bacteria, for example, but also human, animal or plant cells. In addition, however, the method is particularly useful also for isolating/purifying free nucleic acids from samples that do not contain cells or from samples prepared accordingly. More specifically, the method of the invention is suitable, for example, for isolating nucleic acids such as DNA and/or RNA from sample materials of human or animal origin, in particular clinical samples such as blood, plasma, serum, mouth rinse, urine, cerebral fluid, sputum, stool, punctates, epithelial swabs, biopsies and other tissues or bone marrow samples. More specifically, the method of the invention is suitable for isolating fetal DNA from maternal blood samples and in particular plasma. The method of the invention is also suitable in particular for isolating freely circulating nucleic acids such as, for example, tumor DNA and tumor RNA from bodily fluids such as, in particular, plasma and/or serum.

In particular cases, the sample may be employed in the method of the invention without pretreatment. In many cases, however, the sample first needs to be disrupted by a suitable method and the biological material present in said sample be released. Methods for disrupting samples and cells are known to the skilled worker and may be of the chemical, enzymatic or physical kind. It is also possible to combine these methods.

Various factors may prove advantageous for various biological materials in this context; in principle, the following methods are well suited: lysis with the aid of ionic and nonionic detergents such as, for example, SDS, LiDS or sarcosyl, in suitable buffers, the use of chaotropic salts such as, for example, guanidinium hydrochloride (GHCL), guanidinium thiocyanate (GTC), guanidinium isothiocyanate (GITC), sodium iodide, sodium perchlorate, and others; mechanical tearing apart, for example by means of a French press, ultrasound, milling with glass balls, nickel balls, aluminum or in liquid nitrogen; enzymatic lysis, for example with lysozyme, proteinases, proteinase K or cellulases or by means of other commercially available enzymes for lysis;

lysis of the cells by means of bacteriophages or viral infections; freeze-drying; osmotic shock; microwave treatment; temperature treatment; for example heating or boiling or freezing, for example in dry ice or liquid nitrogen, and thawing; alkaline lysis.

As discussed, the above methods are state of the art with regard to lysis and are well known and therefore need not be discussed in detail.

When purifying freely circulating nucleic acids such as, for example, DNA from a blood sample, for example for purifying fetal DNA from a maternal sample, first the cells and other solid components of the blood are removed (for example by centrifugation), and the plasma thus obtained is processed further. Said plasma is usually free of cells and contains the freely circulating nucleic acid, for example maternal and fetal DNA. The purification of free nucleic acids from plasma does not require actual cell lysis in order to release the nucleic acids because the latter are already in a freely circulating form. This also applies to other samples which contain free nucleic acids that accordingly are not located inside cells. However, freely circulating nucleic acids may be in a complex with proteins and/or other substances. For this reason, the nucleic acid-containing starting material, for example plasma, is first treated with a release buffer which ensures that the nucleic acids are released from the complexed form. Function and composition of the release buffer are similar to that of a lysis buffer which is employed for cell disruption; the release buffer generates suitable conditions in the sample for releasing the nucleic acids, and as a result the latter are not present by way of a complex. The addition of the release buffer renders the nucleic acid more accessible to purification. The method of the invention may accordingly also be employed for cell-free starting materials. Depending on its composition, the corresponding release buffer may also work as lysis buffer in order to effectively purify or concentrate nucleic acids. Normally, the usual lysis buffers may also be employed as release buffers.

According to the invention, the use of release or lysis buffers containing chaotropic agents is particularly effective. Even more so since the composition of the release or lysis buffer also influences the conditions under which the nucleic acids bind to the support material. The binding conditions in the sample, which are crucial according to the invention for the efficacy of the method of the invention, may therefore also be adjusted by choosing the release or lysis buffer, for example, in combination with a binding buffer in a suitable manner. Release or lysis buffers according to the present invention contain a chaotropic compound such as, for example, GTC or GHCL, and, where appropriate, a detergent such as SDS or Tween, for example. These agents may be present in aqueous solution or in a buffer solution, i.e. as "release buffer" or "lysis buffer". The buffer employed may be any suitable buffer such as, for example, tris, bicine, tricine or phosphate buffer. Alternatively, the lysis or release agent may also be added separately. Suitable concentrations and amounts of the lysis or release agents vary depending on the respective systems, type of cells, etc. and may be determined by the skilled worker. For specific applications, in particular purification of fetal DNA from blood samples, concentrations in the range from 2 to 7 M, for example, of chaotropic compounds such as, for example, GTC, GHCL or NaI or sodium perchlorate, 0.1 M to 1 M of alkaline agents such as, for example, NaOH, and 0.1 to 50% by weight (w/v) of detergents, in particular nonionic detergents such as Tween, for example, have proved to be useful.

Chaotropic compounds are also present in the sample mixture during binding of the nucleic acids to the support material. The chaotropic compounds may be, for example, from the lysis or release buffer and/or are added separately, however, for example in the form of a binding buffer. Ultimately, the binding conditions in the sample during binding of the nucleic acids to the support material are crucial. Here, the chaotropic compound may be present ultimately up to the limit of solubility. The use of chaotropic compounds is advantageous for efficient binding of the nucleic acid. The concentration of the chaotropic compounds in the sample during binding is preferably in a range from 1 to 10 mol/l, particularly preferably from 2 to 6 mol/l. Examples of suitable compounds are sodium iodide, sodium perchlorate, guanidinium thiocyanate, guanidinium isothiocyanate and guanidinium hydrochloride. The interaction of the concentration and type of the chaotropic compound used and of the alcohol concentration in adjusting the binding conditions has already been discussed in detail above. We refer to the above disclosure.

The sample may also have detergents such as, for example, nonionic detergents and in particular Tween during binding. Said detergents may either be added with the release/lysis buffer or be part of the binding buffer. Detergents cause efficient solubilization of various components in the sample, for example of serum and plasma components. This may prevent the nucleic acid-binding support material from blocking. This is particularly advantageous when a silica membrane is employed.

As discussed, the concentration of the alcohol in the sample during binding of the nucleic acids to the support material is crucial in the method of the invention. Preference is given to employing short-chain branched or unbranched alkanols having from 1 to 5 carbon atoms, such as methanol, ethanol, propanol, isopropanol, butanols or pentanols, for example. Mixtures of the corresponding alcohols may also be employed. Particular preference is given to employing isopropanol or an alcohol or alcohol mixture having isopropanol-like properties. The concentration of the alcohol varies depending on the binding step (binding step (x) for depleting the long-chain nucleic acids, or binding step a) for binding the short-chain nucleic acids).

If the long-chain nucleic acids are depleted in a preliminary step (x), alcohol concentrations are used which promote binding of the long-chain nucleic acids to the support material in order to be able to remove these nucleic acids thereby from the sample. The interaction of the concentration of chaotropic compound and the alcohol concentration has already been discussed in detail above. We refer to the above disclosure. The breakthrough or the supernatant contains a higher proportion of the desired short-chain nucleic acids due to said depletion.

In order to promote binding of the long-chain nucleic acids in step (x) and thus to improve depletion, the concentration of the alcohol during binding of the nucleic acids to the support material is below 30% (v/v) according to the invention. Particularly good results are achieved if the concentration of the alcohol is ≤25%, particularly preferably ≤20% (v/v). Long-chain nucleic acids in particular are bound well under these conditions. This is true in particular in the presence of ≥1 mol/l of chaotropic compounds, preferably ≥2 mol/l, in particular ≥2.4 mol/l. Moreover, the concentration of chaotropic agent for depleting the long-chain nucleic acids is preferably ≤4 mol/l, more preferably ≤3.5 mol/l, even more preferably ≤3.2 mol/l, and most preferably ≤3.1 mol/l. The preferred concentration of the chaotropic compound in the sample moreover depends on the type and/or strength of said chaotropic compound. Particularly strong chaotropic agents such as, for example, guanidinium thiocyanate should be employed at a lower concentration in order to promote binding of the longer-chain nucleic acids (but not of the short-chain nucleic acids). In step (x), guanidinium hydrochloride is preferably employed at a concentration of ≥2.5 mol/l and ≤3.1 mol/l with an alcohol concentration of between 15 and 25%, preferably of approx. 20%, in order to bind the longer-chain nucleic acids and thus deplete them in step (x).

Step a) of the 2-step method employs a higher alcohol concentration for preferred binding of the short-chain nucleic acids. To improve binding of the short-chain nucleic acids, the alcohol concentration in the sample during binding is preferably ≥15% (v/v), ≥19% (v/v), and in particular in a range from approx. 19 to 36%. At concentrations above approx. 25% (v/v), short-chain nucleic acids were even found to be able to be enriched over long-chain nucleic acids, in particular when said nucleic acids had been depleted previously. This applies in particular to adjusting the concentration of chaotropic compounds; suitable concentrations are described above. When higher alcohol concentrations of ≥25% (v/v) are employed in step (a), weaker chaotropic compounds such as guanidinium hydrochloride, for example, or lower concentrations of a stronger chaotropic compound are employed. Accordingly, when using a lower alcohol concentration of ≤25% (v/v) in step (a), a higher concentration of chaotropic compounds, or else a more strongly chaotropic compound such as guanidinium isothiocyanate or guanidinium thiocyanate, is correspondingly employed. This result is particularly advantageous for purifying extracellular nucleic acids such as, for example, fetal DNA from blood samples, since the samples such as, for example, maternal plasma, normally predominantly contain long-chain nucleic acids. The method of the invention can therefore achieve even a more effective purification and even enrichment of the short-chain nucleic acids.

According to one embodiment, the sample mixture contains approx. 30% (v/v) alcohol during binding of the nucleic acids to the support material for preferred binding of the short-chain nucleic acids. This provides an effective method for enrichment of short-chain nucleic acids, achieving >2-fold, >5-fold or even more than 10-fold enrichment of the short-chain nucleic acids. In general, the enrichment potential of the method may be determined by comparing the yields of a 200 bp nucleic acid fragment and a 1000 bp nucleic acid fragment. As a result, the method of the invention is also clearly superior to the methods of the prior art.

According to one embodiment of the 1- or 2-step method, the alcohol in the sample mixture in step (a) is at a concentration which is selected from the group consisting of
≥19% (v/v);
≥25% (v/v);
≥25 to ≤50% (v/v);
≥25 to ≤40% (v/v);
≥19 to ≤36% (v/v);
≥19 to <35% (v/v);
≥15 to ≤25 (v/v);
≥25 to ≤35% (v/v);
≥25 to ≤32% (v/v);
≥28 to ≤32% (v/v).

In the 2-step method which comprises depleting the long-chain nucleic acids in step (x), the concentration of the chaotropic compounds in step a) is the concentration of chaotropic compounds in step (x). Markedly better results are achieved by increasing the alcohol concentration rather than decreasing the concentration of chaotropic compounds at the transition from method step (x) to method step a). Preference is given to employing in the actual isolation step a) even a higher concentration of chaotropic compounds and a higher alcohol concentration than in step (x) in order to promote binding of the short-chain nucleic acids to the support material.

According to one embodiment, the method of the invention has at least one of the following features:
that the concentration of the chaotropic compounds in the mixture in step (x) and/or step (a) is ≥1 mol/l up to the limit of solubility; and/or
that the concentration of the chaotropic compounds in the mixture in step (x) and/or step (a) is ≥2 mol/l, ≥2.4 mol/l or ≥2.6 mol/l; and/or
that the concentration of the chaotropic compounds in step (a) is ≥ the concentration of chaotropic compounds in step (x); and/or
that the nucleic acid-containing starting material is treated beforehand with a lysis buffer; and/or
that the nucleic acid-containing starting material does not contain any cells and no cell lysis is carried out; and/or
that the nucleic acid-containing starting material is treated beforehand with a release buffer; and/or
that no phenol extraction is carried out; and/or
that the isolated nucleic acids are treated with DNase; and/or
that at least 30% of short-chain nucleic acids can be isolated by means of the method; and/or
that at least 50% of short-chain nucleic acids can be isolated by means of the method; and/or
that at least 60% of short-chain nucleic acids can be isolated by means of the method; and/or
that at least 2-fold enrichment of the short-chain nucleic acids is achieved; and/or
that at least 5-fold enrichment of the short-chain nucleic acids is achieved; and/or
that at least 10-fold enrichment of the short-chain nucleic acids is achieved; and/or
that short-chain nucleic acids of a particular length are isolated and/or enriched which are selected from the group of nucleic acids of ≤500 bp, ≤400 bp and/or ≤300 bp and/or ≥50 bp and/or ≥100 bp in length; and/or
extracellular nucleic acids are isolated.

The nucleic acid-binding support material is preferably a nucleic acid-binding solid phase from the group of siliceous materials, silica gel, silicon dioxide, glass, zeolite, aluminum oxide, titanium dioxide, zirconium dioxide, kaolin, gelatinous silica, ceramics or polymeric support materials and polystyrene beads. Ultimately important is the fact that the support material is capable of binding nucleic acids. Particular preference is given to employing silica materials. The use of both silica membranes and magnetic particles having a silica or glass surface has proved useful here. The latter may essentially be bead-like or spherical and preferably have a particle size in the range from 0.02-30 μm, preferably 0.05-15 μm, and particularly preferably from 0.1-10 μm. Magnetic silica particles which may be employed advantageously in the method of the invention are described, for example, in the international application WO 01/71732, the entire contents of which are hereby incorporated by reference.

After the support matrix has been incubated with the nucleic acid-containing material, the nucleic acids are removed from the remaining sample fluid. This is usually achieved by separating the nucleic acids bound according to the invention to the particles—when using magnetic silica particles, with the aid of a magnetic field. For example, the magnetic particles may be drawn to the wall of the vessel in which the incubation had taken place. The liquid containing the ingredients of the sample that have not bound to the magnetic particles may then be removed. In step (x), the supernatant would be processed further (the long-chain nucleic acids are bound to the magnetic particles); in step a), the short-chain nucleic acids are bound to the magnetic particles and, where appropriate after washing steps, optionally eluted from the particles in step b). The processing depends on the type of vessel in which the incubation has taken place. Examples of suitable method steps for removing the liquid are those of removing the liquid by decanting, pipetting, filtering or aspirating.

As discussed, it is also possible to employ silica membranes, for example. Liquids may be removed here by centrifugation or by applying vacuum or by pressure. The nucleic acids to be purified are present at low concentrations in large volumes in many applications of the method of the invention, in particular when purifying fetal DNA from maternal blood samples. The use of a silica membrane in the prior art often incurs the problem of large sample volumes possibly blocking the membrane. According to the method of the invention, however, this problem does not occur because special buffer substances/buffer concentrations are employed. It is particularly advantageous here if detergents are employed.

Examples of nucleic acids which may be isolated by the present method are DNA, RNA, mRNA, mitochondrial, epigenetically modified, single-stranded, double-stranded, circular, plasmid, cosmid, artificial or synthetic nucleic acids, and also cDNA and fragments thereof. The method of the invention is particularly suitable for enriching short-chain nucleic acids (for example DNA and RNA in any form, including noncoding RNA such as, for example, miRNA, or synthetic nucleic acids) of ≤1000 bp, ≤800 bp, ≤500 bp, or ≤300 bp in length. According to one embodiment, short-chain nucleic acids of any particular length are isolated and/or enriched that are selected from the group of nucleic acids of ≤500 bp, ≤400 bp, ≤300 bp and/or ≥50 bp, ≥100 bp in length. Preference is given to purifying DNA and/or RNA. DNA or RNA of ≥50 nucleotides in length can be purified particularly efficiently. To obtain short-chain RNA, the purified nucleic acid is preferably treated with DNAse.

The size of the isolated nucleic acids may also be varied/controlled by choosing the alcohol concentration, in particular in combination with the concentration of chaotropic agents. Both variants (1-step method and 2-step method) of the method of the invention enable also short-chain nucleic acids to be isolated effectively. The short-chain nucleic acids may also be specifically enriched by appropriately adjusting the binding conditions, as described herein. The method is particularly suitable for enrichment of fetal nucleic acids, as evidenced also by the examples hereinbelow.

The method of the invention may therefore be employed advantageously in order to isolate extracellular nucleic acids such as, for example, fetal DNA from maternal blood. The present invention therefore also provides a method for enrichment of fetal nucleic acids from a blood sample, in particular from plasma or serum, which method is characterized in that the method of the invention for isolating/purifying short-chain nucleic acids is carried out. Details of said method are specified above.

Further fields of application, however, can be found for example in forensics and in other fields in which the purification of small nucleic acids is crucial. In addition, the method of the invention may also be employed in diagnostics, for example for purifying freely circulating tumor nucleic acids from a sample such as blood, for example.

The present invention also provides a method for enriching nucleic acids from a sample but not for enriching fetal nucleic acids from a blood sample, which method is characterized in that the method of the invention for isolating/purifying short-chain nucleic acids is carried out. Details of said method are specified above.

The method of the invention is particularly suitable for the use in diagnostics. It can also be automated and therefore employed for use on corresponding purification robots.

The invention also provides a kit for isolating and/or purifying nucleic acids, in particular short-chain nucleic acids, from a nucleic acid-containing starting material, said kit comprising buffers and/or reagents and optionally at least one nucleic acid-binding support material for carrying out the method of the invention. Details of said method are specified above.

A corresponding kit may be used for purifying fetal DNA from a blood sample. In addition, a corresponding kit is provided for purifying short-chain nucleic acids from a sample, but not for enriching fetal DNA from a blood sample.

The kits of the invention can be employed in particular in the field of diagnostics and for medical applications. They may be employed in an automated manner.

FIG. 9 is a table indicating various reaction conditions under which nucleic acids bind to support material according to a 1-step method as described in Example 5.

EXAMPLES

The present invention will now be illustrated on the basis of examples. The experiments were carried out on the basis of the experimental protocols described hereinbelow.

The starting point for applying the method of the invention to isolating freely circulating fetal DNA from maternal blood with concomitant enrichment of said fetal DNA over the maternal DNA is the finding, described in the literature, that the average length of the two nucleic acid species differs. While the average length of fetal DNA is currently assumed to be shorter than 500 bp, the average length of maternal DNA is longer than 500 bp.

Example 1: Assay for Determining the Average Length of Fetal and Maternal DNA

Three different plasma pools produced from blood of women pregnant with male fetuses were used for investigating the size distribution of the freely circulating DNA therein. Said plasma pools were pools A, B and C. Pool A included plasma from blood samples of pregnant women in the first to third trimester of pregnancy. Pools B and C in each case included plasma from blood taken from the pregnant women in the first and second trimesters of pregnancy; at a time when there are still relatively low amounts of freely circulating fetal DNA but which has relatively high relevance in terms of the time of clinical diagnosis.

The starting materials used were 10 ml of plasma and, in the case of pool A, 5 ml of plasma. The procedure was according to the QIAamp Blood DNA Midi protocol (QIAGEN) adapted to a volume of 10 ml. 300 µl of AE buffer (QIAGEN, commercially available) were used in each case for elution. Elution was followed by ethanol/sodium acetate precipitation, and the dried pellet was resuspended in 15 µl of buffer EB (QIAGEN, commercially available). After agarose gel electrophoresis, the individual size fractions were excized from the gel, and a gel extraction was carried out according to the QIAquick vacuum protocol for gel extraction. For each gel fraction, elution was into 100 µl; in the subsequent PCR, in each case 20 µl of the eluates were used in duplicates. Amplification was carried out using appropriate primers, firstly the SRY locus for detecting the freely circulating fetal DNA. SRY is detectable only in male individuals. Since only blood from pregnant women which surely carry a male fetus was used, all SRY signals were attributable to DNA of fetal origin. Amplification was also carried out using appropriate primers of the c-myc locus for detecting the total freely circulating DNA in the maternal blood. Said amplification was carried out on an ABI 7500 instrument (Applied Biosystems). The result therefrom is depicted in FIG. 1 and FIG. 2.

Figure 1:
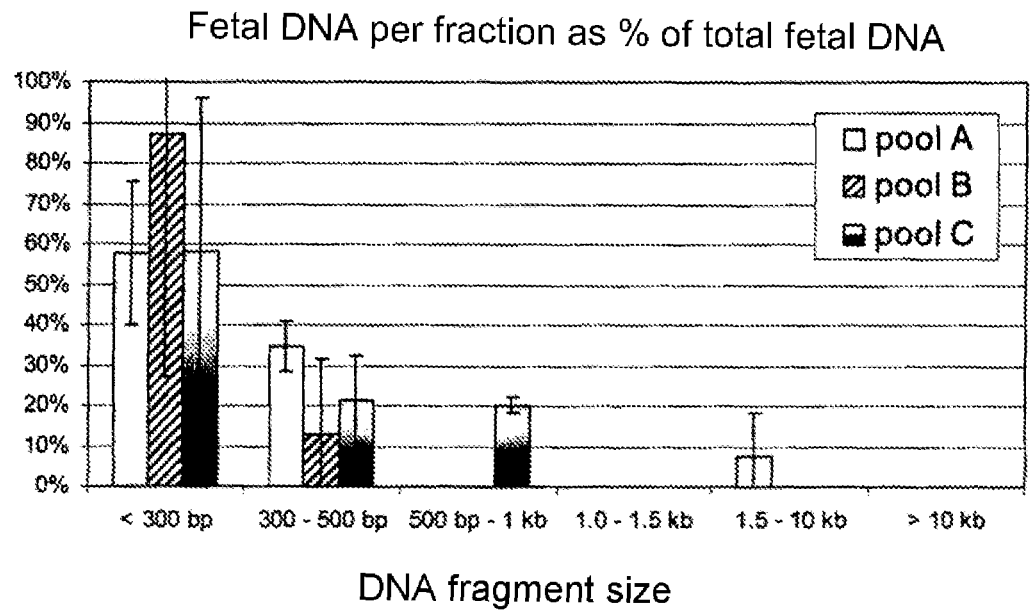
FIG. 1 shows the size distribution of fetal DNA as a function of the pools used in Example 1.

FIG. 1 depicts the size distribution of fetal DNA as a function of the pools used.

Figure 2:
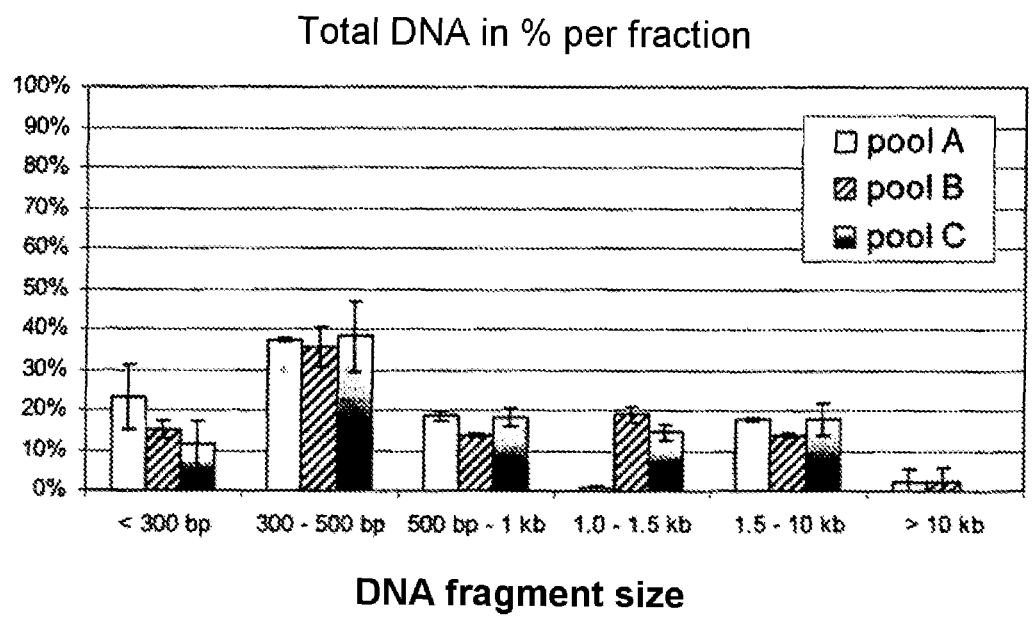
FIG. 2 shows the size distribution of total DNA as a function of the pools used in Example 1.

FIG. 2 depicts the size distribution of total DNA as a function of the pools used.

This experiment demonstrates that the fetal DNA is present only by way of short fragments, as described in the literature. The majority is clearly within the fraction of less than 300 bp, a significant portion exhibiting fragment lengths of from 300 to 500 bp. Only a very small proportion of the freely circulating fetal DNA in the maternal blood is longer than 500 bp. On the other hand, not all of the maternal DNA is larger than 500 bp. About half of the maternal DNA freely circulating in the blood is likewise only 500 bp in length and shorter, but the other half is markedly longer than 500 bp. Consequently, a significant, relative enrichment of fetal DNA over maternal DNA can be achieved by means of a size fractionation of the isolated/enriched nucleic acids.

Example 2

In order to simulate the different size distribution of fetal DNA (the majority being shorter than 300 bp, see example 1) and maternal DNA (mainly longer than 500 bp), two different PCR amplicons were added as background to the plasma. A 219 bp fragment should simulate the fetal DNA, and a fragment of 1018 bp in length should simulate the maternal DNA. In a first experiment, relatively high amounts of said PCR amplicons were used for this, namely in each case $2\times10^6$ copies in 600 µl of plasma. The procedure was according to the following protocol:

To 600 µl of plasma in a 5 ml vessel, 90 µl of protease (QIAGEN) and 600 µl of buffer AL (QIAGEN, commercially available) which contains guanidine were added. After mixing by vortexing, the mixture was incubated for lysis at 56° C. for 15 min. After lysis, the PCR amplicons of 219 or 1018 bp in length were added to the lysate. The binding conditions were adjusted with 100 µl of isopropanol so as to result in a concentration of 6.9% (w/v) isopropanol in the total sample.

Mixing by vortexing was followed by incubation at room temperature for 10 min. For binding, 50 µl of MagAttract magnetic particles with silica surface (QIAGEN) were added, and the mixture was allowed to bind on a shaker for 5 min. After binding, the particles were separated from the supernatant by means of a magnet, and the supernatant was removed. The supernatant was stored at 4° C. until further treatment.

Treatment of MagAttract Particles

After removal of the supernatant, the magnetic particles were mixed with 750 µl of buffer AW1 (QIAGEN, commercially available) on a plate shaker for 5 min, and the particle suspension was then transferred to a 1.5 ml reaction vessel. After magnetic separation in this vessel, the supernatant was removed and discarded. The particles were then also washed consecutively with 750 µl of buffer AW2 (QIAGEN, commercially available) and 750 µl of ethanol (in each case after 5 min of incubation on a shaker). After the washing with alcohol, the particles were dried in a heating block at 56° C. for 10 min. The nucleic acids bound to the particles were eluted by using 200 µl of RNase-free water (QIAGEN), with said elution being carried out by shaking again for 5 min. The eluate was transferred to a new vessel after magnetic separation.

Treatment of the Supernatant of the Binding

The supernatant/breakthrough of the binding (the material not bound to the magnetic particles) was worked up as follows. The supernatant after binding was admixed with 2 ml of buffer B6 (2.5 M GuHCl, 50% isopropanol), resulting in a concentration of isopropanol of 32.4% (v/v), mixed by vortexing and incubated at room temperature for 10 min.

After incubation, 50 µl of MagAttract particles were added, with the procedure being the same as described for the first binding mixture (washing with AW1 (QIAGEN, commercially available), AW2 (QIAGEN, commercially available), ethanol, elution in RNase-free water). Alternatively, 2 ml of 100% isopropanol (buffer B11) were added to the supernatant after binding, thus resulting in a concentration of isopropanol of 61.9% (v/v). Equal aliquots were removed from the eluates, and a 119 bp amplicon was amplified with the aid of a real-time PCR, which amplicon results in an identical fragment both from the 219 bp fragment and from the 1018 bp fragment. The amplicon was detected with the aid of SYBR Green during the PCR.

Figure 3:
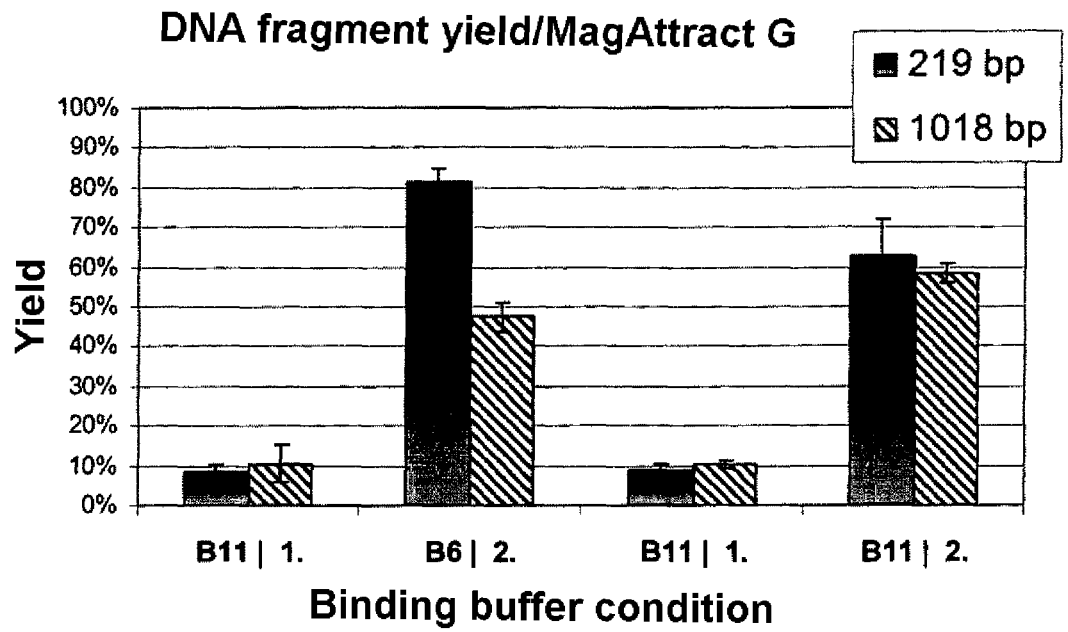
FIG. 3 shows DNA fragment recovery using Buffer B11 or B6 and MagAttract G as described in Example 2.

This resulted in the image depicted in FIG. 3.

This experiment demonstrates that, under the chosen binding conditions, only little nucleic acid both of the 219 bp fragment and of the 1018 bp fragment binds to the first MagAttract particles, in each case about only 10%. Readjusting of the binding conditions with buffer B6 or B11, however, surprisingly results in a difference in the yield depending on the fragment size. While, with the aid of buffer B6, more than 80% of the short DNA (representing the fetal DNA) can be recovered, the result for the longer DNA (representing the maternal DNA) is only a yield of about 50%. Using buffer B11, in contrast, does not result in any substantial differences in the yield between the two DNA fragment lengths.

This experiment demonstrates that the fetal DNA can be enriched over the maternal DNA with the aid of a two-step binding system with the aid of two solid phases under suitable conditions, with only very small losses in the yield of fetal DNA being recorded.

Example 3

The procedure was as described in example 2, but this time only 200 000 copies of the defined fragments were used in order to simulate a more realistic picture of the actual freely circulating copy numbers in the blood. This time, binding to the matrix under the first condition was carried out using 100 µl of buffer B11 (see above)+1.2 ml of buffer B6, thus resulting in a concentration of isopropanol of 20.3% (v/v) (see above). For an alternative condition for binding to the matrix, 100 µl of buffer B11 and 2.0 ml of buffer B6 were added to the plasma lysate. In addition, the DNA fragments were bound under the two abovementioned buffer conditions in the binding mixture in each case to a MagAttract matrix or QIAamp Mini columns.

Figure 4:
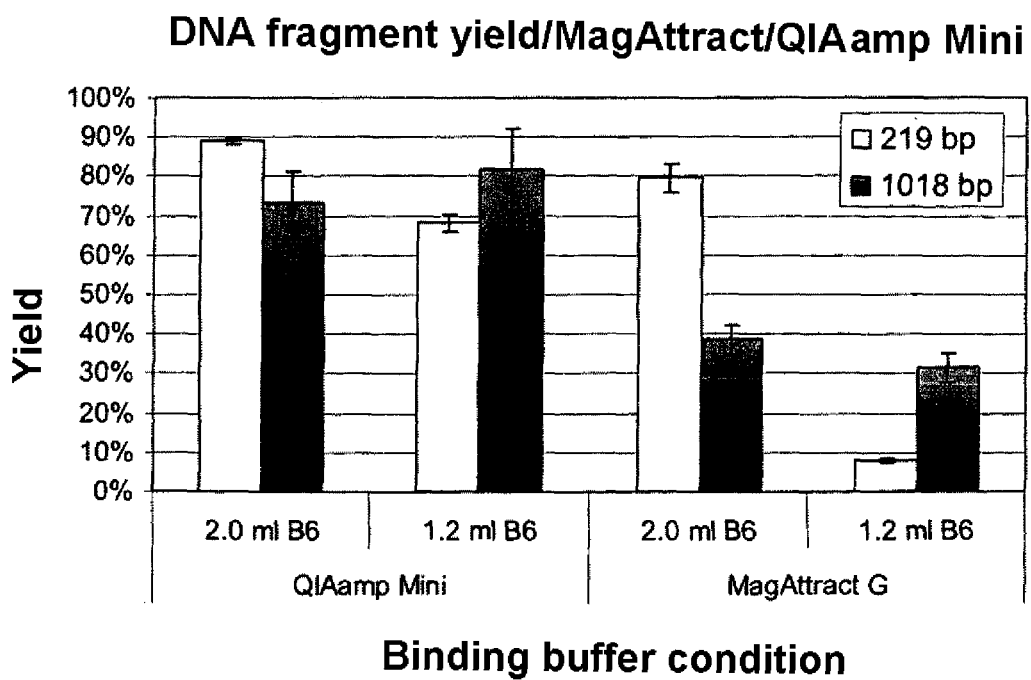
FIG. 4 shows DNA fragment recovery using different amounts of Buffer B6 and QIAamp Mini or MagAttract G at the second step of a two-step isolation method as described in Example 3.

The procedure for this was as follows. Buffers B11 and B6 were added to the supernatant, mixed and incubated at room temperature for 10 min. The lysate of two samples was combined and applied to a QIAamp Mini column (QIAGEN) with the aid of an extension tube (QIAGEN) in vacuo. Washing was carried out successively with 1000 µl (for binding to MagAtract particles) or 750 µl (for binding to QIAamp Mini columns) of AW1 (QIAGEN, commercially available), AW2 (QIAGEN, commercially available) and ethanol. For drying, the columns were centrifuged at 14 000 rpm for 3 min and put in a heating block at 56° C. for 5 min. The MagAttract particles were treated as described in example 2. Elution was carried out here too with 200 µl of RNase-free water (centrifugation at 14 000 rpm for 1 min). The subsequent real-time PCR here produced the image depicted in FIG. 4.

This experiment surprisingly shows that, with the same buffer composition, there is hardly any difference, whether magnetic particles or a silica membrane is employed as solid phase. The addition of 1.2 ml of buffer B6 leads to relatively long DNA fragments (approx. 1000 bp) being enriched in the DNA sample obtained, while surprisingly and conversely short DNA fragments (approx. 200 bp) are enriched with the addition of 2.0 ml of buffer B6. When using a silica membrane (QIAamp Mini), the yield of DNA is higher than with MagAttract particles overall, but the size-dependent DNA binding is also slightly less prominent. Consequently, a combination of magnetic particles (first matrix) and silica membrane (second matrix) in a two-step DNA extraction (in which the DNA-containing supernatant of the first binding is used further and bound to a silica membrane) is outstandingly suited to efficiently enrich short DNA fragments in two steps and therefore also to effectively enrich fetal DNA over maternal DNA on the second matrix.

Example 4

Figure 5:
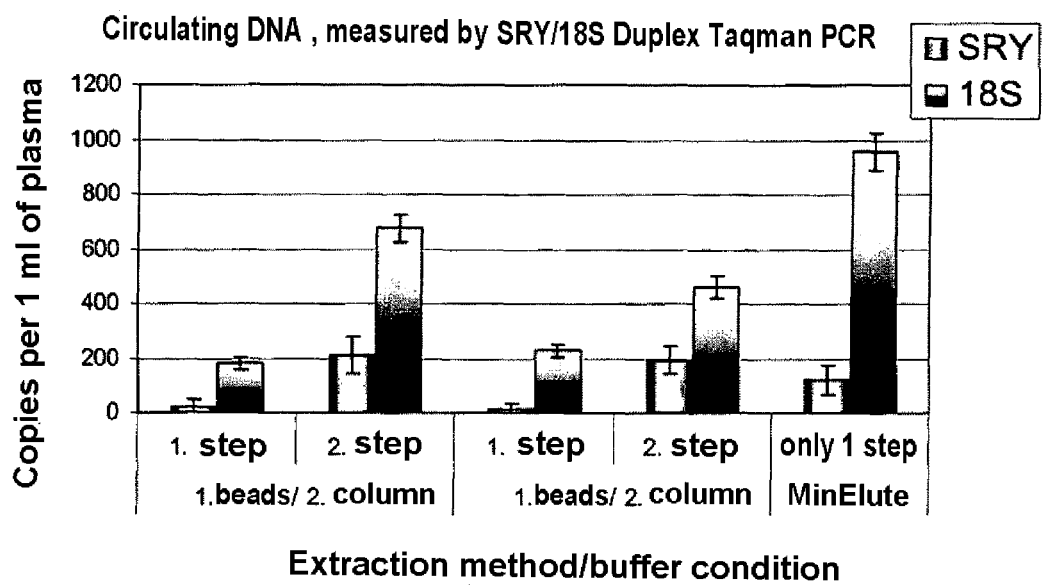
FIG. 5 shows copy numbers of fetal DNA (SRY) and maternal DNA (18S) per ml of plasma using different extraction methods and buffer conditions as described in Example 4.

The procedure was similar to that indicated in example 3 but this time a real blood sample was used and a two-step binding method was employed. This involved adding 1.2 ml of buffer B6 to the sample for the first binding step and subsequently adjusting the breakthrough or supernatant of the first binding step with additional buffer B6 to 2.0 ml of buffer B6 in total. The starting material was a pool of plasma samples of pregnant women of the first and second trimesters, which were reliably carrying a boy. The fetal DNA was detected by amplifying the SRY locus in the subsequent real-time PCR, with total DNA being detected by amplifying the 18S locus (see also example 1). For comparison, a one-column protocol was carried out according to the QIAamp MinElute Virus Vacuum protocol which corresponds to the prior art. The results are depicted in FIG. 5.

Figure 6:
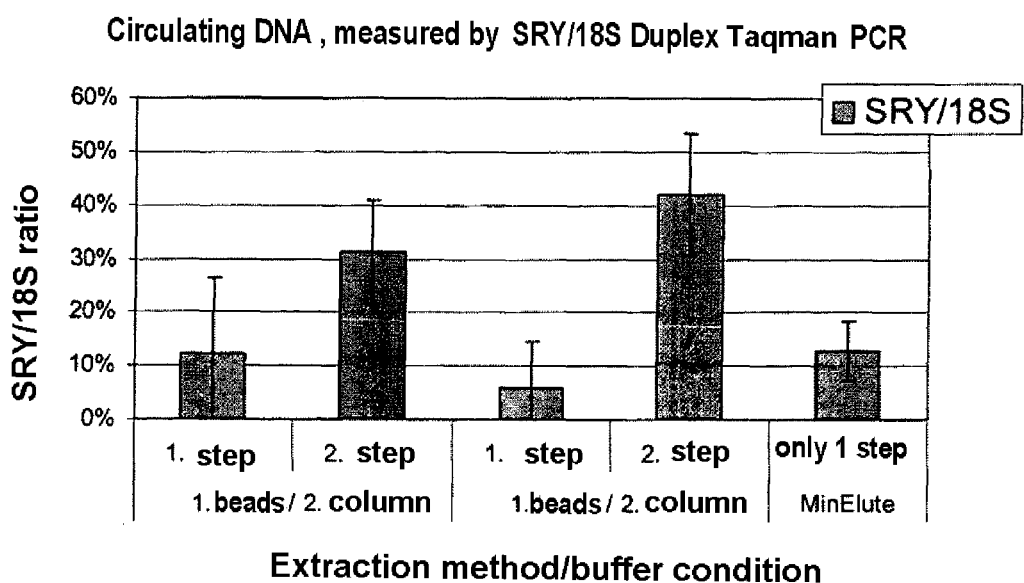
FIG. 6 shows fetal DNA (SRY) to maternal (18S) DNA ratio of DNA isolated using different extraction methods and buffer conditions as described in Example 4.

The result of this experiment matches the result of example 3, demonstrating that the artificial system with 219 bp and 1018 bp fragments is a good simulation of the real situation (example 4). While practically no fetal DNA is lost through the first matrix, significant amounts of maternal DNA already bind to said first matrix (here: MagAttract magnetic particles). Maternal DNA is therefore effectively depleted in this step (x) and thus is already depleted during purification through the second column. Compared to the prior art (MinElute 1-step), the two-matrix method not only produces an increased absolute number of fetal DNA but, due to the at least partial depletion of maternal DNA through the first matrix, also results in a markedly better ratio of fetal to maternal DNA in the eluate, clearly advancing the detectability of fetal genetic material from maternal blood. FIG. 6 illustrates once more the improved ratio of fetal to maternal DNA. While the one-step purification according to the prior art results in a proportion of about 15% fetal DNA in the eluate (quantified by SRY/18S duplex real-time PCR), the proportion with a two-step purification is more than twice that, at from 30 to 40%.

Example 5

Figure 7:
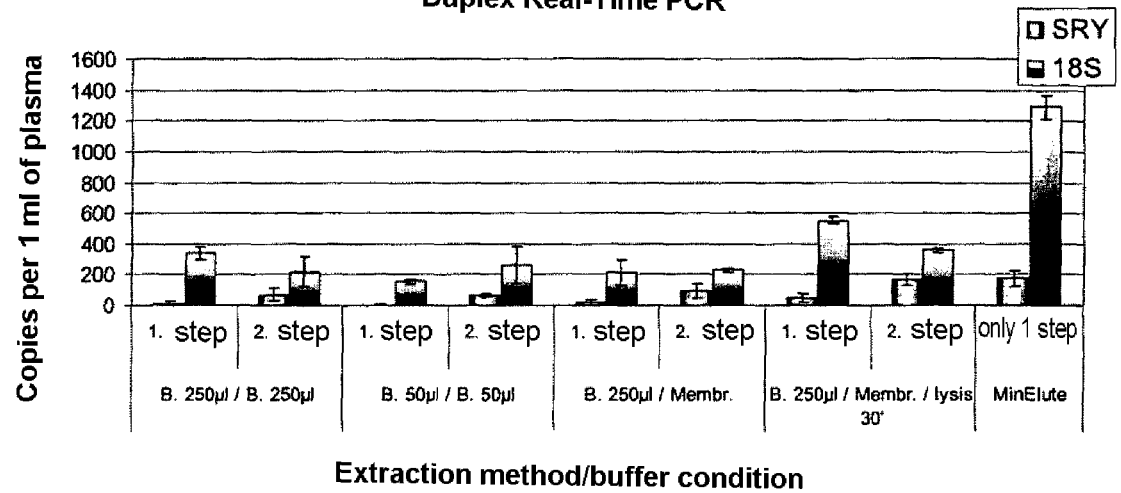
FIG. 7 shows copy numbers of fetal DNA (SRY) and maternal DNA (18S) per ml of plasma using different extraction methods and buffer conditions as described in Example 5.
Figure 8:
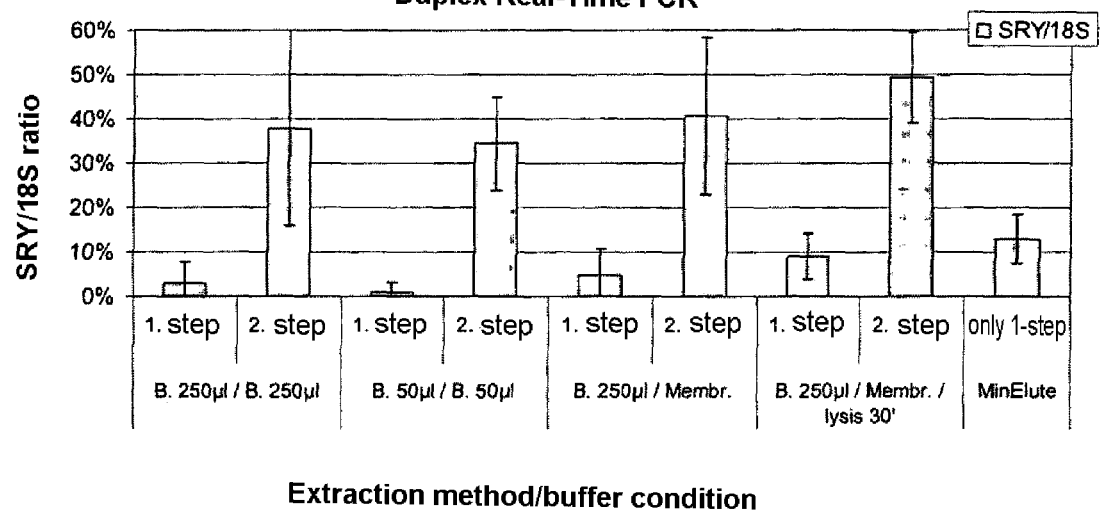
FIG. 8 shows fetal DNA (SRY) to maternal (18S) DNA ratio of DNA isolated using different extraction methods and buffer conditions as described in Example 5.

The procedure was as described in example 4 but this time a higher volume of plasma was used (3 ml per reaction mix). In addition, various combinations of binding surfaces (MagAttract particles and QIAamp Mini columns) and various amounts of MagAttract were compared to one another. Additionally, lysis in the membrane 2-step protocol lasted 30 min rather than only 15 min. The results are depicted in FIG. 7. This experiment confirms the results of the previous experiments. Compared to the 1-step protocol of the prior art, the 2-step protocol according to the invention always produces improved ratios of fetal DNA to maternal DNA, independently of whether magnetic particles with a silica surface or silica membranes are used in the second binding step. An extended lysis of 30 min here appears to improve still further the ratio of fetal DNA to maternal DNA in favor of fetal DNA, thereby enabling the maternal DNA to be markedly depleted. Said improvement of the ratio is also depicted in FIG. 8.

While the 1-matrix protocol according to the prior art results only in a ratio of fetal to maternal DNA of about 15%, this ratio can be increased to up to 50% fetal DNA by the 2-matrix protocol. The proportion of fetal DNA in the purified circulating DNA from maternal plasma can thus be markedly increased in comparison with the prior art.

Figure 10:
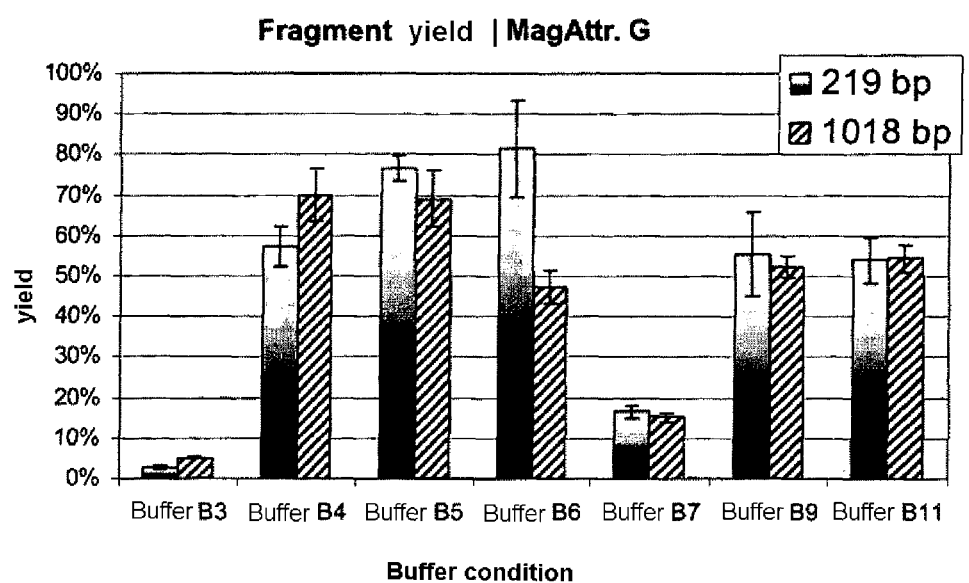
FIG. 10 shows DNA fragment recovery using different reaction conditions shown in FIG. 9 and MagAttract.

The table depicted in FIG. 9 also indicates various reaction conditions in the sample, under which the nucleic acids bind to the support material (according to the 1-step method of the invention). MagAttract particles were employed as support material. The results are depicted in FIG. 10.

Example 6

In order to compare the efficiency of the method of the invention for extracting freely circulating DNA from human plasma, the following protocols were compared with one another:
1. The 1-step method of freely circulating DNA, employed in the prior art, namely the modified QIAamp MinElute Virus protocol specified below
2. The 1-step protocol according to the present invention for extracting/isolating freely circulating DNA ("one step").

This experiment employed and tested pooled plasma of male donors in four extraction repeats per protocol. DNA was extracted according to the particular protocol. 5 ml of plasma were used; the DNA was eluted into 50 µl.

1. QIAamp MinElute Virus Vacuum Protocol, Modified—Prior Art

The freely circulating nucleic acids were isolated from 5 ml of EDTA plasma. The protocol was carried out as follows:

Release Conditions

750 µl of QIAGEN protease (dissolved in Protease Solvent) were pipetted into a 50 ml vessel. Subsequently, 5 ml of plasma and 5 ml of the guanidine-containing buffer AL (with 5.6 µg of carrier RNA) were added. The vessel was closed and vortexed well in order to obtain a homogeneous solution. Said homogeneous solution was then incubated in a water bath at 56° C. for 30 minutes.

Addition of Marker Fragments

To the homogeneous mixture were then added 20 µl of a marker fragment mixture in order to simulate the situation of fetal nucleic acid mixed with maternal nucleic acids. For this purpose, in each case 200 000 copies of 219 bp (corresponding to fetal DNA) and 1018 bp (corresponding to maternal DNA) fragments were added.

Binding 6 ml of ethanol were added to the lysate. The mixture was vortexed and incubated on ice for 5 minutes. The lysate was loaded onto a QIAamp Mini column, with an extension tube being attached to a QIAvac 24 vacuum apparatus. The lysate was pulled through the column by applying said vacuum. The extension tubes were carefully removed.

Washing Steps

600 µl of buffer AW1 (QIAGEN, commercially available) were applied to the column and vacuum was applied. This washing step was repeated with 750 µl of buffer AW2 (QIAGEN, commercially available) and with 750 µl of ethanol.

The columns were placed in 2 ml collection tubes, and centrifuged at 14 000 rpm for 3 minutes. The columns were then transferred to fresh collection tubes and dried in a heating block at 56° C. for 10 minutes.

Elution

The dried columns were placed in 1.5 ml vessels, and 50 µl of buffer AVE (QIAGEN, commercially available) were applied to each column; incubation for 3 minutes and centrifugation at 14 000 rpm for 1 minute.

The nucleic acids obtained in this manner are present in the eluate.

2. Isolation of Freely Circulating Nucleic Acid According to the 1-Step Method of the Invention Release 750 µl of QIAGEN Protease (dissolved in Protease Solvent) were pipetted into a 50 ml vessel. 5 ml of plasma and 5 ml of the guanidine-containing lysis/release buffer AL (QIAGEN, commercially available, without carrier RNA) were added.

The vessel was closed and vortexed well in order to form a homogeneous solution. Said homogeneous solution was incubated in a water bath at 56° C. for 30 minutes.

Addition of Marker Fragments

Here too, again 20 µl of a marker fragment mixture were added (in each case 200 000 copies of 200 bp and 1000 bp fragments in order to simulate the ratio of fetal to maternal DNA).

Binding

The following binding conditions were then adjusted by adding binding buffer: approx. 25 to 35% isopropanol and more than 2M chaotropic compounds. The reaction conditions in the overall sample rather than in the buffer are important, since the reaction conditions in the mixture are crucial for the binding efficiency of the short-chain nucleic acids to the support material.

The sample was vortexed and incubated on ice for 5 minutes.

The lysate mixed with the binding buffer was then loaded onto a QIAamp Mini column with extension tube attached to a QIAvac 24 vacuum apparatus. The lysate was pulled through the column by applying vacuum. The extension tubes were then carefully removed.

Washing Steps

600 µl of a washing buffer such as, for example, AW1 (QIAGEN, commercially available) were applied to the column and removed by means of vacuum. Further washing steps with 750 µl of buffer AW2 (QIAGEN, commercially available) and with 750 µl of ethanol may follow.

The washed columns were placed in 2 ml collection tubes and centrifuged at 14 000 rpm for 3 minutes. The columns were then placed in fresh collection tubes and dried in a heating block at 56° C. for 10 minutes.

Elution

The columns were placed in 1.5 ml vessels, and 50 µl of elution buffer AVE (QIAGEN, commercially available) were applied to the columns, incubation was carried out for 3 minutes, followed by a centrifugation step at 14 000 rpm for 1 minute. The mainly short-chain nucleic acids are present in the eluate.

3. Results

The yield of DNA according to the individual protocols was measured by quantitative, duplex real-time PCR, with Taqman samples being used (4 PCR repeats per DNA extraction). The DNA was determined firstly by a Y-chromosomal target (DYS14) and an 18S rDNA-specific target. Both methods ultimately determined the concentration of DNA in the sample. Since the 18S rDNA is present on both chromosomes, twice the amount of it is present than of the Y-chromosomal target. The DNA yield was indicated by way of haploid genome copies per ml of plasma.

The enrichment of small DNA fragments was determined independently in the enriched 200 bp and 1000 bp DNA fragments in a duplex real-time PCR.

Figure 11:
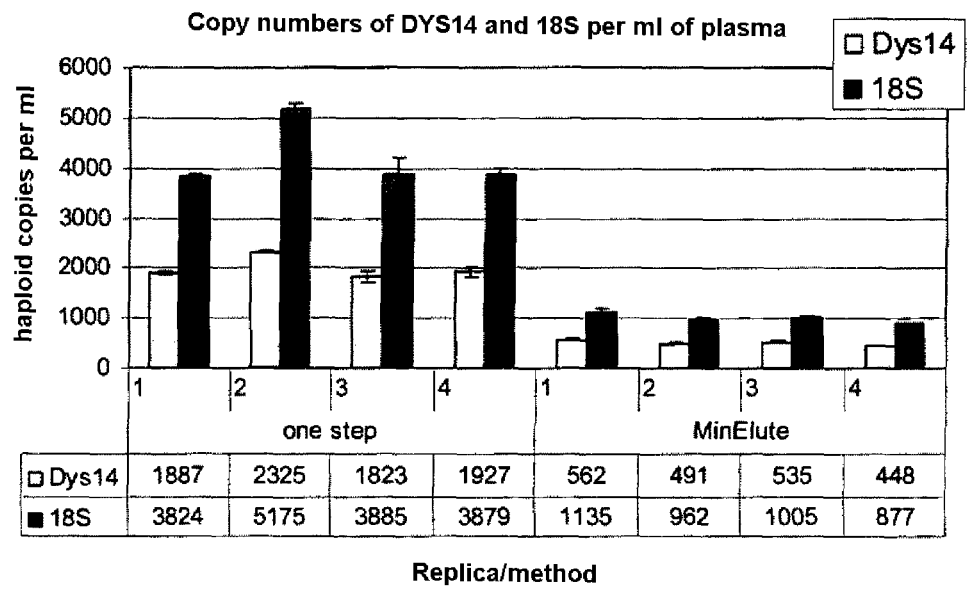
FIG. 11 shows copy numbers of DYS14 and 18S per ml of plasma using a one-step method disclosed herein and a one-step method known in the prior art (MinElute) as described in Example 6.

The results are depicted in FIG. 11 ff.

FIG. 11 depicts the DNA yield per sample (4 samples were assayed for each extraction method). Therefore, the total DNA content obtained by means of the individual methods is shown. As the overview indicates, the 1-step method of the invention achieves a distinctly higher yield than the 1-step method (MinElute) known in the prior art. The DNA yield is many times higher, and this is a particular advantage especially for determining nucleic acids with low expression/presence.

Figure 12:
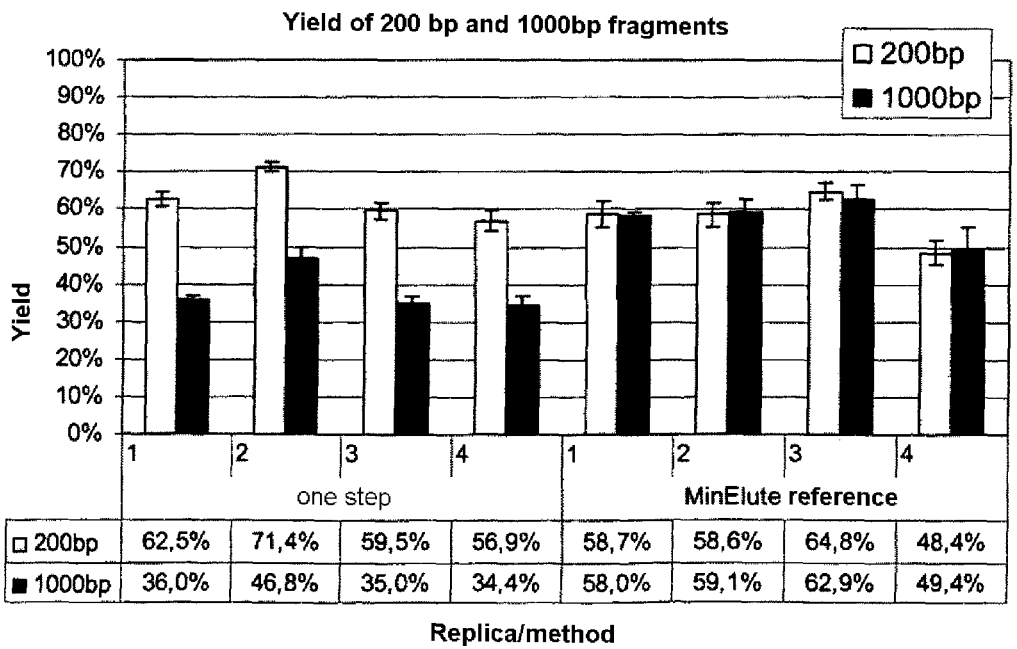
FIG. 12 shows the yield of fed-in 200 bp (simulating fetal nucleic acids) and 1000 bp (simulating long-chain maternal fragments) DNA fragments using a one-step method disclosed herein and a one-step method known in the prior art (MinElute) as described in Example 6.

FIG. 12 depicts the yield of the fed-in 200 bp (simulating fetal nucleic acids) and 1000 bp (simulating long-chain maternal fragments) DNA fragments. As discussed above, the 200 bp and 1000 bp fragments were fed in in a 1:1 ratio, namely 200 000 copies each. The graph depicted in FIG. 12 indicates, whether the ratio of short-chain to long-chain nucleic acids is still 1:1 for the purified nucleic acids, or whether the short-chain nucleic acids were enriched. As FIG. 12 demonstrates, the 1-step method of the prior art (MinElute) has a ratio of long-chain to short-chain nucleic acids of approx. 1:1. The short-chain nucleic acids are therefore not enriched. Below FIG. 12, a table also indicates how many of the individual fragments (200 bp and 1000 bp) were obtained from the sample. Thus, for example, the information that 62.5% of 200 bp fragments and 36% of 1000 bp fragments were purified indicates that 62.5% of the initially fed-in 200 000 copies of the 200 bp fragments and 36% of the 200 000 copies of the 1000 bp fragments were purified and thus isolated. As shown, the short-chain nucleic acids are clearly enriched over the long-chain nucleic acids by the 1-step method of the invention. The ratio is no longer 1:1 (as fed in) but substantially more short-chain nucleic acids were purified and thus enriched in the eluate. The method of the invention is therefore clearly superior to the prior art.

Figure 13:
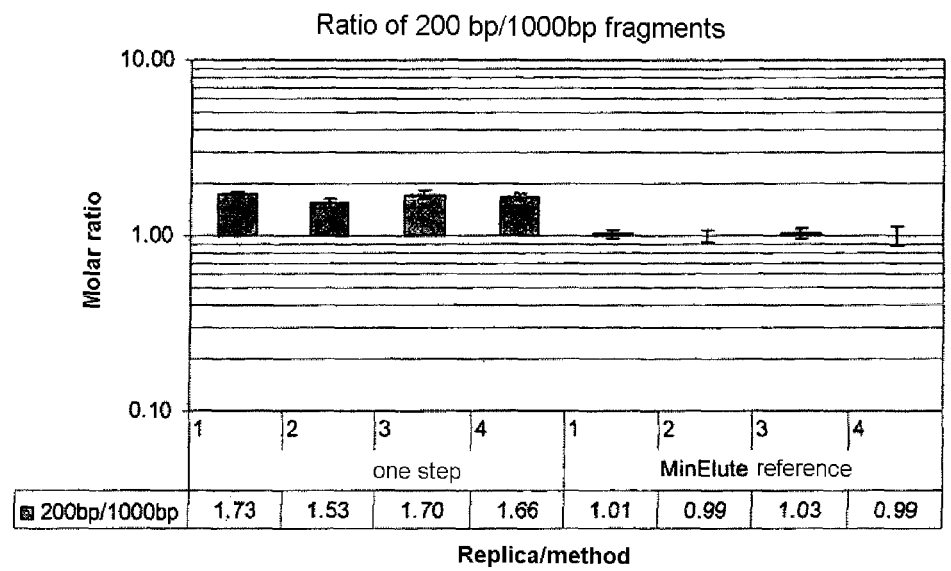
FIG. 13 shows molar ratios of fed-in 200 bp to 1000 bp DNA fragments using a one-step method disclosed herein and a one-step method known in the prior art (MinElute) as described in Example 6.

The ratio of the purified 200 bp to 1000 bp fragments is additionally depicted in FIG. 13. While the 1-step method known in the prior art achieves values of approximately 1, the ratio in the 1-step method of the invention has clearly shifted in the direction of the short-chain nucleic acids which accordingly are preferentially enriched/isolated. The 2-step method of the invention, in which the long-chain nucleic acids are initially depleted in a preliminary step, even achieves a 5- to 10-fold enrichment.

The 1-step method of the invention is clearly superior to the 1-step method known in the prior art, as the results indicate. The 1-step method of the invention enriches small nucleic acids during preparation, which can be attributed to the unique reaction conditions during binding which lead to preferred binding of short-chain nucleic acids.

Example 7

The isolation of nucleic acids, in particular of circulating RNA from 5 ml of plasma or serum, is described below.

1350 µl of buffer AVE (QIAGEN, commercially available, contains guanidine) are added to a vessel containing 1350 µg of lyophilized carrier RNA, thereby producing a 1 µg/µl solution. Said 1 µg/µl solution is then mixed with buffer AL (QIAGEN, commercially available, contains guanidine). The mixing ratio is adjusted depending on the number of samples. For the treatment of a single sample, 8.5 ml of buffer AL are mixed with 5.6 µl of buffer AVE. For more samples, the ratios must be adapted accordingly. The vessel is moved back and forth 10 times for mixing.

6 ml of protease solution (QIAGEN, commercially available) is added to a lyophilized QIAGEN Protease (7.5 A.U, commercially available) and mixed carefully.

500 µl of QIAGEN Protease are pipetted into a 50 ml vessel (tube), and the 5 ml of plasma are added. Thereafter, 8.5 ml of buffer AL, mixed with carrier RNA (see above), are added, and the substances are mixed by vortexing.

The mixed sample is incubated at 56° C. for 30 minutes.

7.5 ml of a binding buffer are added to the lysate (containing approx. 0.5 to 1.5 mol/l guanidinium, preferably around 1 mol/l, and isopropanol, approx. 60-90% (v/v); preferably more than 70%). The mixture is vortexed for 30 seconds and incubated on ice for 5 minutes. A QIAamp Mini column is inserted into a VacConnector on a QIAvac 24 Plus, with an extension tube being placed in the open QIAamp Mini column.

The lysate is introduced into the extension tube, and vacuum is applied. As soon as the lysate has been pulled through the columns, the vacuum pump is switched off and the pressure is equalized. The extension tube is discarded.

The column is removed from the vacuum support and transferred to a 2 ml collection vessel. The column is centrifuged at 14 000 rpm for 1 min.

For RNA preparation, a 10 µl DNAse I stock solution is pipetted to 70 µl of buffer RDD (QIAGEN, commercially available). Mixing is carried out by moving the tube. The RDD buffer is provided with the RNAse-free DNAse set (QIAGEN, CAT. No. 79254).

The columns are again placed on the QIAvac 24 Plus vacuum support. The DNAse I mixture is pipetted directly onto the QIAamp Mini silica gel membrane and incubated at moderate temperatures (20 to 30° C.) for 15 minutes.

Subsequently, 600 µl of buffer AW1 (QIAGEN, commercially available) are pipetted onto the QIAamp Mini column. Vacuum is then applied in order to draw the mixture through the column. This is followed by adding 750 µl of buffer AW2 (QIAGEN, commercially available) which are pulled through the column by applying vacuum.

Subsequently, 750 µl of ethanol (96-100%) are applied to the column and pulled through by means of vacuum. The QIAamp Mini column is then removed from the vacuum support and the VacConnector is discarded. The columns are placed in a clean 2 ml collection vessel and centrifuged at 20 000×g, 14 000 rpm for 3 minutes.

The column is placed in a new 2 ml collection vessel and dried at 56° C. for 10 minutes, with open lid. The QIAamp Mini column is then placed in a clean 1.5 ml microcentrifugation vessel, and the collecting vessel is discarded. 20 to 60 µl of buffer AVE (QIAGEN, commercially available) are pipetted in the center of the QIAamp Mini membrane. This is followed by incubation for 3 min, with closed lid.

This is followed by a centrifugation step at 20 000×g, 14 000 rpm, for 1 min in order to elute the RNA. An RNAse inhibitor is then added.

Short-chain RNA can be purified using the corresponding protocol.

Example 8

Another preferred variant of the 1-step method is described below, in which alcohol concentrations of less than 25% (v/v) are employed.

This variant is particularly suitable for isolating circulating DNA and (m)RNA from 5 ml of plasma, serum or another cell-free body fluid. This method was utilized hereinbelow in order to purify circulating nucleic acids from 5 ml of plasma (see FIG. 14).

Lysis

Approx. 1.7 to 2.2 mol/l guanidinium thiocyanate and 7.5 to 9 (w/v) of detergent are used during lysis.

To this end, 500 µl of QIAGEN Proteinase K are pipetted into a 50 ml tube and 5 ml of plasma are added. 4.0 ml of ACL buffer (QIAGEN, containing 5.6 µg of Carrier RNA) are added, the cap is closed, followed by mixing by pulse vortexing for 30 s.

The sample is heated to 60° C. and incubated for 30 min. The tube is spun briefly to remove drops from the inside of the lid.

Binding

Between 2.1 and 2.5 mol/l guanidinium thiocyanate, 9% to 11% (w/v) detergent and 19% to 21% (v/v) isopropanol are used during binding. To this end, 9.0 ml of buffer ACB buffer (QIAGEN) are added to the lysate, the lid is closed, and the solution is mixed thoroughly by pulse vortexing for 15-30 s. The mixture is incubated on ice for 5 min.

A column (QIAamp Mini Column) may be employed for purification. The column is placed in a VacConnector, and a 20 ml extension tube is placed in the open column. The extension tube must be inserted tightly into the column to prevent a loss of sample. The lysate is introduced into the extension tube of the column and the vacuum pump is switched on. After the complete lysate has been pulled through the column, the vacuum pump is switched off and the pressure is reduced to 0 mbar. The extension tube is carefully removed.

Washing

600 µl of buffer ACW1 (QIAGEN) are applied to the column for washing. The lid of the column is left open and the vacuum pump is switched on. After the entire buffer ACW1 has run through the column, the vacuum pump is switched off and the pressure is reduced to 0 mbar.

750 µl of buffer of washing buffer ACW2 (QIAGEN) are applied to the column. The lid of the column is left open and the vacuum pump is switched on. After the entire buffer ACW2 has run through the column, the vacuum pump is switched off and the pressure is reduced to 0 mbar.

Subsequently, 750 µl of ethanol (96-100%) are applied to the column. The lid of the column is left open and the vacuum pump is switched on. After all of the ethanol has run through the column, the vacuum pump is switched off and the pressure is reduced to 0 mbar.

The lid of the column is closed and the column is placed in a clean collecting tube. The column is then centrifuged at full speed (20 000×g, 14 000 rpm) for 3 min.

Elution

The column is placed in a new 2 ml collecting tube, the lid is opened and the compound is incubated at 56° C. for 10 min to dry the membrane completely.

The column is placed in a clean 1.5 ml elution tube, and the collecting tube is removed. 20-150 µl of elution buffer (AVE buffer, QIAGEN) are applied to the center of the column membrane. The lid is closed, followed by incubation at room temperature for 3 min.

The nucleic acids are eluted by centrifuging at full speed for 1 min (20 000×g; 14 000 rpm). The eluate contains both circulating DNA and RNA.

Figure 14:
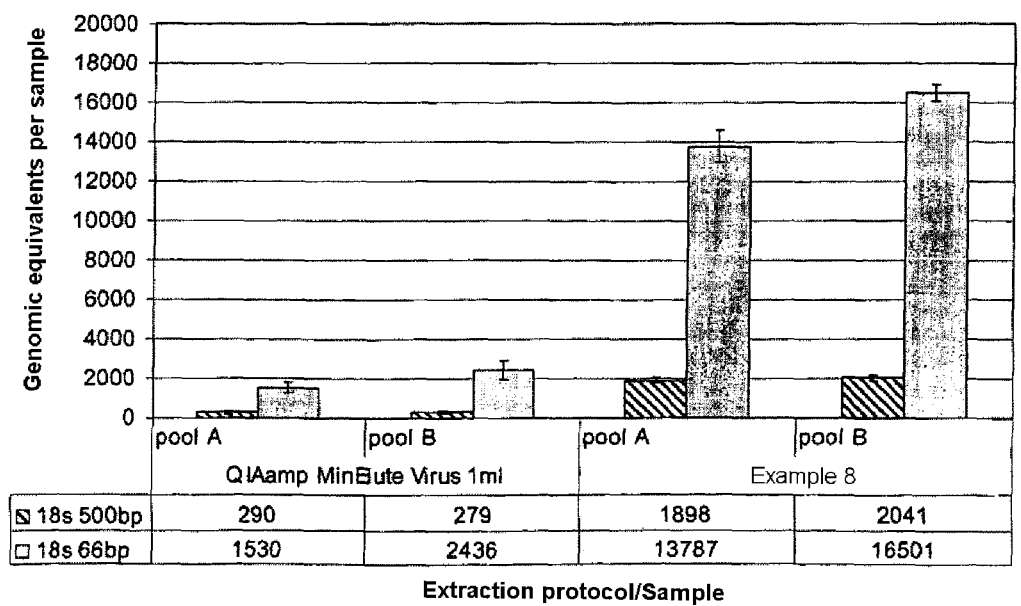
FIG. 14 shows yield of circulating DNA extracted from plasma according to the protocol of Example 8 and quantified by a duplex real-time PCR.

FIG. 14 depicts the results of the purification according to the protocol of example 8. Freely circulating cell-free DNA was purified according to the protocol of example 8 (5 ml of pooled plasma) and the QIAamp MinElute Virus vacuum kit (1 ml of plasma) as reference. The elution volume was 100 µl. The DNA yield was quantified by a duplex real-time PCR, using a 500 bp and a 66 bp target sequence in the coding region for 18S ribosomal RNA. The real-time PCR was carried out using the QuantiTect Multiplex PCR kit. Six replica nucleic acid extractions were carried out for each condition. As seen, the protocol according to example 8 achieves a higher yield of circulating DNA compared to a conventional method corresponding to the prior art. The yield here is markedly higher than would be expected merely on the basis of the higher sample volume.

Example 9

Example 9 shows a preferred method for purifying RNA from samples, in particular plasma, serum or other body fluids. The concentrations listed below are designed for a 5 ml sample.

Figure 15:
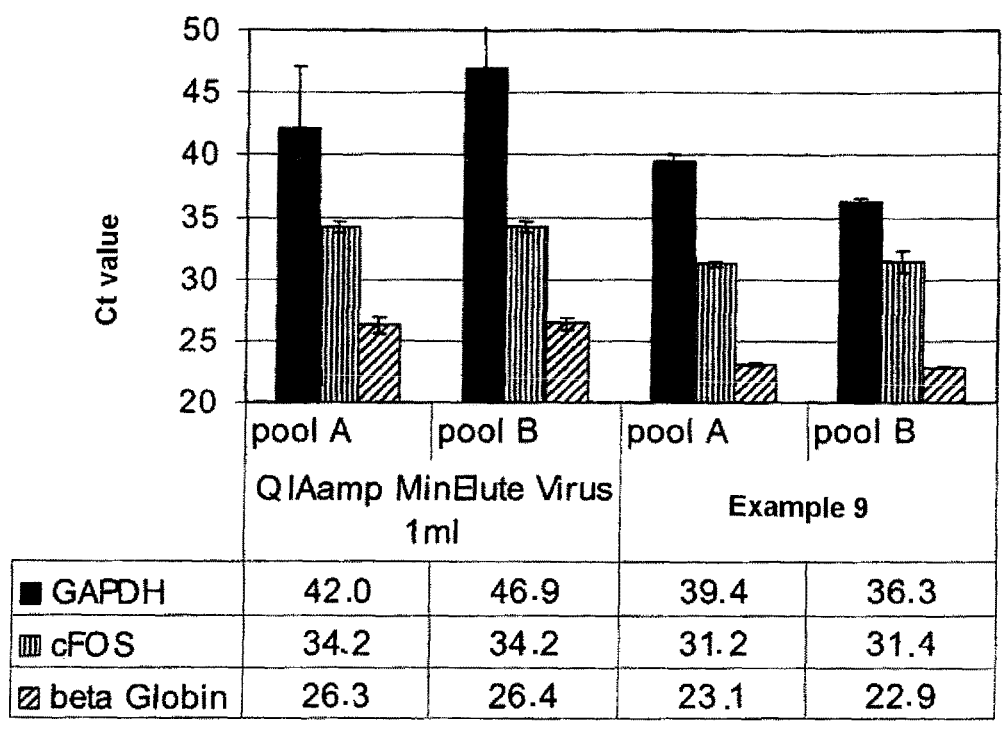
FIG. 15 shows Ct values of real-time RT-PCR using freely circulating cell-free RNA purified according to Example 9 as templates.

The following protocol was employed for purifying RNA from 5 ml of plasma (see FIG. 15).

The method here is carried out as described in example 8. However, in order to selectively purify RNA, a DNAse step in which DNA is digested using DNAse I is carried out after binding and before the washing steps are carried out:

The column is transferred to a 2 ml collecting tube and centrifuged at 14 000 rpm for 1 min. This step removes lysate residues which could hinder DNAse digestion. For each sample, 10 µl DNAse stock solution are added to 70 µl of buffer RDD (QIAGEN) and mixed by inverting the sample.

The columns are returned to their original positions. The DNAse I incubation mix (80 µl) is applied to the silica gel membrane of the small column and incubated at moderate temperatures (20-30° C.) for 15 min.

This is followed by washing and eluting as described in example 8.

The results are depicted in FIG. 15. Freely circulating cell-free RNA was purified according to example 9 (5 ml of plasma; including DNAse treatment of the QIAamp column according to the protocol) and purified by the QIAamp MinElute Virus vacuum kit (1 ml of plasma) as reference. The elution volume was 100 µl. The RNA yield was quantified by real-time RT-PCRs which were specific for GAPDH, c-fos, and beta-globin mRNAs. The real-time RT-PCR was carried out using the QuantiTect Multiplex RT-PCR kit. For each condition, six replica nucleic acid extractions were carried out.

The lower Ct values ("cycle of threshold") indicate that the method protocol according to example 9 achieves a higher yield of circulating mRNA compared to a conventional method corresponding to the prior art. The yield here is markedly higher than would be expected merely on the basis of the higher sample volume.

The invention claimed is:

1. A method for isolating and/or purifying extracellular nucleic acids from an extracellular nucleic acid-containing starting material, comprising:

(a) binding the extracellular nucleic acids to a nucleic acid-binding support material by contacting the starting material with said nucleic acid-binding support material in the presence of at least one chaotropic compound and at least one branched and/or unbranched alcohol, said alcohol being present at a concentration of ≥15% (v/v) and ≤35% (v/v);

(b) optionally eluting the bound extracellular nucleic acids from the nucleic acid-binding support material.

2. The method of claim 1, wherein in step (a), the alcohol is present in the mixture at a concentration of ≤25% (v/v).

3. The method of claim 1, wherein the concentration of the chaotropic compound in step a) is ≥2 mol/l and ≤3.5 mol/l, and said chaotropic compound is selected from the group consisting of thiocyanates, isothiocyanates and perchlorates.

4. The method of claim 1 having one or more of the following features:
   a. the concentration of the chaotropic compounds in the mixture in step (a) is ≤4 mol/l, ≤3.5 mol/l, ≤3.2 mol/l or ≤3.1 mol/l; and/or
   b. the at least one chaotropic compound in step (a) is a thiocyanate, isothiocyanate or perchlorate; and/or
   c. at least 30%, at least 50%, or at least 60%, of the extracellular nucleic acids present in the starting material can be isolated by the method; and/or
   d. extracellular nucleic acids selected from the group of nucleic acids of ≤500 bp, ≤400 bp and/or ≤300 bp and/or ≥50 bp and/or ≥100 bp in length are isolated and/or concentrated.

5. The method as claimed in claim 1, wherein the extracellular nucleic acid to be isolated/purified is DNA.

6. The method of claim 1, wherein the nucleic acid-binding support material is selected from the group consisting of siliceous materials, silicon dioxide, silica gel, glass, zeolite, aluminum oxide, titanium dioxide, zirconium dioxide, kaolin, gelatinous silica, magnetic particles, in particular magnetic silica or glass particles, ceramics, and polymeric support materials, or wherein the nucleic acid-binding support material is selected from the group consisting of silica membrane and magnetic particles having a silica surface or a glass surface.

7. The method of claim 1, wherein the method is for isolating and/or concentrating extracellular nucleic acids from a bodily fluid.

8. The method according to claim 7, wherein the bodily fluid does not contain cells or is prepared not to contain cells.

9. The method according to claim 7, wherein the bodily fluid is selected from blood, plasma, serum, urine and/or cerebral liquor.

10. The method according to claim 9, wherein the method is for isolating and/or concentrating extracellular nucleic acids from a blood sample.

11. The method of claim 10, wherein the extracellular nucleic acids are fetal nucleic acids.

12. The method according to claim 1, wherein the alcohol is isopropanol.

13. The method according to claim 1, wherein no phenol extraction is carried out.

14. The method according to claim 1, wherein the extracellular nucleic acids are double-stranded.

15. The method according to claim 1, wherein the alcohol concentration in step a) lies in a range of ≥15% (v/v) and ≤25% (v/v) and that the concentration of the chaotropic compound in step a) is ≥2 mol/l.

16. The method according to claim 15, wherein the chaotropic compound is guanidine thiocyanate or guanidine isothiocyanate.

17. The method according to claim 1, wherein the nucleic acid-binding support material is located in a column, wherein optionally, the nucleic acid-binding support material is a silica membrane.

18. The method according to claim 1, wherein during binding one or more detergents are present.

19. The method of claim 18, wherein the one or more detergents comprise a non-ionic detergent.

20. The method according to claim 1, wherein the method is for isolating extracellular nucleic acids selected from fetal DNA, tumor DNA and tumor RNA from plasma and/or serum.

21. The method according to claim 1, wherein the method is not for concentrating fetal nucleic acids from a blood sample.

22. The method according to claim 1, wherein the extracellular nucleic acids are single-stranded.

* * * * *